(12) United States Patent
Abothu et al.

(10) Patent No.: US 12,383,230 B2
(45) Date of Patent: Aug. 12, 2025

(54) COMPOSITE ACOUSTIC ABSORBER FOR ULTRASOUND TRANSDUCER ARRAY

(71) Applicant: Siemens Medical Solutions USA, Inc., Malvern, PA (US)

(72) Inventors: Isaac Abothu, Sammamish, WA (US); Stephen Davis, Sammamish, WA (US); Phong Cha, Carnation, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 842 days.

(21) Appl. No.: 16/197,940

(22) Filed: Nov. 21, 2018

(65) Prior Publication Data

US 2020/0155119 A1     May 21, 2020

(51) Int. Cl.
*G10K 11/162*     (2006.01)
*A61B 8/00*     (2006.01)
*B06B 1/06*     (2006.01)

(52) U.S. Cl.
CPC ......... *A61B 8/4494* (2013.01); *A61B 8/4488* (2013.01); *B06B 1/0622* (2013.01); *G10K 11/162* (2013.01)

(58) Field of Classification Search
CPC ... A61B 8/4494; A61B 8/4488; B06B 1/0622; G10K 11/162
See application file for complete search history.

(56) References Cited

U.S. PATENT DOCUMENTS

| | | | |
|---|---|---|---|
| 5,644,085 A | 7/1997 | Lorraine et al. | |
| 5,942,333 A | 8/1999 | Arnet et al. | |
| 6,104,596 A * | 8/2000 | Hausmann | H01L 21/6833 279/128 |
| 8,354,773 B2 * | 1/2013 | Oliver | A61B 8/4483 310/327 |
| 9,827,592 B2 * | 11/2017 | Lee | B06B 1/06 |
| 2011/0178407 A1 | 7/2011 | Lu et al. | |
| 2014/0070668 A1 | 3/2014 | Ona | |
| 2016/0007961 A1 * | 1/2016 | Lee | G10K 11/002 600/459 |

FOREIGN PATENT DOCUMENTS

| | | |
|---|---|---|
| CN | 101675468 | 3/2010 |
| CN | 102183710 | 9/2011 |
| CN | 102460565 | 5/2012 |
| CN | 105252687 | 1/2016 |
| CN | 108135569 | 6/2018 |
| CN | 108807838 | 11/2018 |

(Continued)

OTHER PUBLICATIONS

Yaran, Wang: "Fundamentals of Diagnostic Ultrasonography"; Mar. 30, 2009, pp. 5-6.

(Continued)

*Primary Examiner* — Isam A Alsomiri
*Assistant Examiner* — Abdallah Abulaban

(57) ABSTRACT

Acoustic absorbers are formed for ultrasound transducers. The acoustic absorber provides desired attenuation, impedance, and thermal conductivity qualities based on a filler of rubber, ceramic, and metal particles. The relative amounts of the different fillers may be adjusted to tune the acoustic attenuation, thermal conductivity, and/or acoustic impedance.

18 Claims, 1 Drawing Sheet

(56) References Cited

FOREIGN PATENT DOCUMENTS

| | | |
|---|---|---|
| EP | 589396 A2 | 9/1993 |
| EP | 2974802 A1 | 1/2015 |
| JP | 2007189342 | 7/2007 |
| JP | 2008011494 | 1/2008 |
| JP | 2008118212 | 5/2008 |
| JP | 2009060501 | 3/2009 |
| KR | 20120000696 | 1/2012 |
| KR | 20140032528 | 3/2014 |
| KR | 20150025066 | 3/2015 |

OTHER PUBLICATIONS

Zongwen, Duan et al: "Clinical Ultrasound Medicine"; Jun. 30, 2017, pp. 21-22.

* cited by examiner

COMPOSITE ACOUSTIC ABSORBER FOR ULTRASOUND TRANSDUCER ARRAY

BACKGROUND

The present embodiments relate to acoustic backing for ultrasound transducers. Ultrasound transducers, such as used in medical diagnostic ultrasound imaging, include transducer elements for converting between electrical and acoustic energy. To absorb undesired acoustic energy and prevent receiving echoes from clutter or structures outside of the patient, an acoustically absorptive backing block connects to the transducer. The backing block is formed by attenuate material for absorbing acoustic energy. The higher the attenuation, the more effective in preventing receiving echoes from clutter or structures outside of the patient. Example backing material is a cured epoxy with plastic fillers. The epoxy with plastic filler-based backing block generally has an acoustic impedance that matches the transducer, is somewhat but generally not highly absorptive of ultrasound, and does not provide high thermal conductivity.

Ultrasound transducers have many heat generating elements, such as a two-dimensional transducer having up to 10,000 piezoelectric elements. Higher power operation is often desired but results in acoustic noise and more heat. An acoustic backing material with somewhat absorptive qualities and poor thermal conductivity may impose limits on the use of the transducer.

BRIEF SUMMARY

By way of introduction, the preferred embodiments described below include ultrasound transducers, acoustic absorbers, and/or methods for forming the acoustic absorber. The acoustic absorber provides desired attenuation, impedance, and thermal conductivity qualities based on a filler of rubber, ceramic, and metal particles. The relative amounts of the different fillers may be adjusted to tune the acoustic attenuation, thermal conductivity, and/or acoustic impedance.

In a first aspect, an ultrasound transducer includes an array of transducer elements. The transducer elements of the array are operable separably for transducing between acoustic and electrical energies. The array has a face at which the acoustic energies are transmitted and received and a back opposite the face. The ultrasound transducer also includes a backing adjacent the back of the array. The backing is a composite of rubber, metal, and ceramic particles.

In a second aspect, a composite acoustic absorber is provided for an ultrasound transducer array. The composite acoustic absorber includes cured epoxy with rubber filler, metal filler, and ceramic filler distributed in the cured epoxy.

In a third aspect, a method is provided for forming an acoustic backing of a transducer. An epoxy, rubber powder, ceramic powder, and metal powder are mixed to form a mixture. The mixture is cast into a mold for an acoustic backing block. The mixture in the mold is cured.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A composite acoustic absorber provides high attenuation and high thermal conductivity. Using a combination of metal, rubber, and ceramic fillers distributed to form a homogeneous material may provide both high attenuation, high thermal conductivity, and/or tunable impedance. Unlike metal foam or other absorbers, the absorber may be easily machined. Materials with high thermal conductivity in general have low acoustic attenuation. In addition materials with high density (impedance) also generally have low acoustic attenuation. The combination of three or more different types of filler may provide high acoustic attenuation with good thermal conductivity and desired impedance. Different types particles contribute to different characteristics of the absorber.

Figure 1:
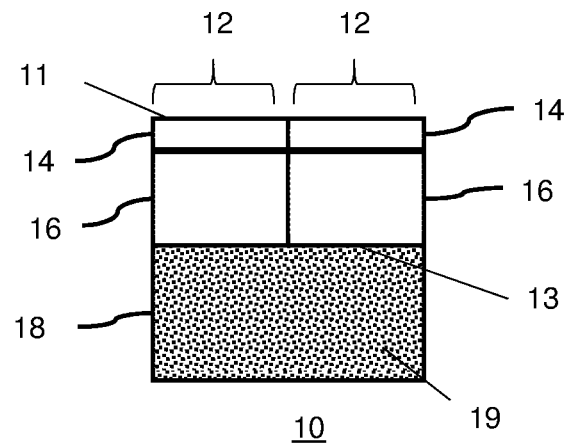
FIG. 1 is an example illustration of a transducer array of elements with a composite backing having three or more fillers.

FIG. 1 shows one embodiment of part of an ultrasound transducer 10. The ultrasound transducer 10 includes an absorber for absorbing acoustic energy and providing a desired impedance and thermal conductivity based on the types of fillers included.

The ultrasound transducer 10 is an array of elements 12. The array is part of a one-dimensional (1D) or multidimensional (e.g., 1.25D, 1.5D, 1.75D, or 2D) transducer. The array 10 is within a transducer probe, such as a handheld probe, catheter, intra-cavity (e.g., transesophageal), or another probe. Only two elements 12 are shown for simplicity, but the array may include additional elements 12, such as tens, hundreds or thousands of elements 12. In a one-dimensional array, 32, 64, 128, 196 or other numbers of elements 12 are arranged as a linear, curved linear, or phased array. In other embodiments, the elements 12 are part of a multi-dimensional array, such as a 1.25D, 1.5D, 1.75D, or 2D array arranged as a flat or curved surface array.

The array has a face 11 at which the acoustic energies are transmitted and received to and from the patient. The face 11 is flat, concave or convex. The face 11 is adjacent an acoustic window of the probe and/or is placed adjacent a region to be scanned. One or more matching layers 14 are at the face 11. Opposite the face of the array 10 is a back 13. The back 13 is away from the acoustic window, such as being further away from the acoustic window than the transducer layer 16. The back 13 of the array 10 is positioned adjacent to backing 18, such as the bottom of the transducer layer 16 as the back 13 of the array.

Each transducer element 12 of the array includes one or more transducer layers 16, one or more matching layers 14, one or more backing layers 18, electrodes, and signal lines (e.g., flex circuits or asperity contact pads connected with respective electrodes). Additional, different or fewer components may be provided. For example, a switch or multiplexer is provided for connecting a same cable or a same transmit channel to different ones of the elements 12 and associated electrodes. As another example, a tuning circuit is provided for each element 12.

Each element 12 is operable for transducing between acoustic and electrical energies. The transducer layer 16, in combination with ground and signal electrodes on opposite sides of the transducer layer 16, converts electrical energy to acoustic energy for transmission. Most of the generated acoustic energy propagates towards the face 11 and back 13 of the array. The transducer layer 16 converts received acoustic energy into electrical energy. The electrodes are provided on opposite sides of the transducer layer 16 for operation of the transducer 10.

The elements 12 are acoustically and electrically isolated for separate operation. Kerfs, epoxy, or other spacing between elements 12 may provide acoustic isolation. A bridge or common transducer material may alternatively be connected between the elements 12. Separate signal electrodes may provide electrical isolation. A common ground electrode may be shared by some or all the elements 12. Multiple elements 12 may share a transmit or receive electrode, such as in a matrix system or a system forming macro elements.

The one or more transducer layers 16 are formed from a same or different transducer material. For example, a single crystal, such as PZN-PT or PMN-PT, is used. Other piezoelectric materials, such as PZT5H, or composite materials may be used. In another embodiment, the transducer layer 16 is formed from a semiconductor material as a microelectromechanical or CMUT device. In yet another embodiment, the transducer layer 16 is formed from an electrostrictive polymer.

All the elements 12 are formed from a same block of transducer material. The transducer layer 16 of each element 12 is a same thickness, number of layers, and material, such as forming the transducer layer 16 for each element 12 by kerfing a block of PZT. The same thickness of the transducer layer 16 between the emitting face 11 and the back 13 is provided. In other embodiments, different elements 12 have different structures, such as a different number of transducer layers 16, different thickness, and/or different materials.

The acoustic impedance of the transducer layer 16 of each element 12 is between 10 and 50 Mrayl. Piezoelectric ceramic has an acoustic impedance of about 30 Mrayl. Different material mixtures or formation processes may result in deviation from 30 Mrayl. "About" accounts for this deviation as well as due to the addition of multiple layers of transducer material or other material. Composite transducer layers 16 (e.g., posts or slabs of piezoelectric material held together or surrounded by epoxy) may have a different acoustic impedance.

The backing layer 18 is adjacent to the back 13 of the array, such as being adjacent to the bottom (as shown in FIG. 1) of the transducer layer 16. Electrodes, such as metalized flexible circuit material, or other layers may be positioned between the transducer layer 16 and the backing layer 18.

The backing layer 18 is a backing block or other composition of acoustic absorber. The backing layer 18 may be a single molded or formed (e.g., machined) block for all the elements 12. Alternatively, separate backing blocks are provided for different groups of elements 12.

The backing layer 18 is shaped and sized to mate with the ultrasound transducer 10. The dimensions of the backing layer 18 along azimuth and lateral dimensions of the array may match the array or extend beyond the array. The depth of the backing layer 18 may be greater than the ¼ of the longest wavelength for which the transducer 10 is to be used. In one embodiment, the depth is greater than the depth of the transducer material layer 16. The backing layer 18 may include protrusions or indentations for mating with the transducer 10. Clips or other structures may be added to mate or connect the backing layer 18 to the transducer 10. Once aligned, the backing layer 10 (e.g., molded block of acoustic absorber) is bonded or fixed to the transducer 10.

The backing layer 18 includes a plurality of different materials. The different materials may be mixed, such as a composite backing. Four or more different types of material form the backing layer 18. A matrix or base material is epoxy, but other bonding agents may be used such as elastomers. The backing layer 18 is formed from a support structure of cured epoxy, such as epoxy with the thermoset and thermoplastic components mixed together to chemically cure. Heat, pressure, or other environmental control may be used to form the cured epoxy.

Other types of material are included as filler 19, such as particles in powder form. Any fillers 19 may be used with different types of material providing different forms of filler. The filler particles have any size, such as being less than 10% of the transducer wavelength in a longest dimension. The filler particles have any size, such as being spherical, prismoid, and/or amorphous. By including the filler within the backing layer 18 (e.g., mixed with the epoxy), a solid block of the matrix (e.g., epoxy) and filler is formed. Alternatively, the filler causes air gaps or pockets to also be included. In either case, the backing layer 18 includes particles held in place and/or separated by epoxy or other matrix material. Each or most particles are surrounded by epoxy or matrix.

Various fillers 19 are distributed with or without air gaps in the epoxy. The filler 19 is formed from three or more different types of material or substances. For example, the filler 19 of the composite of the backing block 18 includes rubber, metal, and ceramic particles. The rubber particles are natural rubber, elastomer, or other rubber material. For example, silicone powder is used. The rubber particles are of any range of sizes (maximum diameter), such as 1-10, 8-100, 20-80, 40-50 micrometers, or other range. The particles may be a powder and/or have a spherical or amorphous shape.

The metal particles are any metal. For example, tungsten, copper, or aluminum powder is used. The metal particles are of any range of sizes (maximum diameter), such as 1-10, 10-60, 20-50, 30-40, or 15-25 micrometers. The particles may be a powder and/or have a spherical, prismoid, or amorphous shape.

The ceramic particles are any inorganic compound of metal, non-metal, or metalloid, such as crystalline oxide, nitride or carbide material. Carbon or silicon material may be used as the ceramic particles. In one embodiment, the ceramic particles are an aluminum nitride powder. The ceramic particles are of any range of sizes (maximum diameter), such as such as 1-10, 8-100, 20-80, 40-50 micrometers, or other range The particles may be a powder and/or have a spherical, prismoid, or amorphous shape.

The filler 19 is distributed throughout the backing layer 18. The distribution of filler is substantially homogeneous. The distribution of each type of filler and matrix is substantially homogeneous. "Substantially" is used to account for tolerance in the mixing process, such as any sub-volume of 10% or more of the backing layer 18 having variation from other sub-volumes of the backing layer 18 of less than 4%. Each element 12 has backing with a similar composition to other elements 12 due to the homogeneous distribution of the different fillers.

Any amount of filler 19 relative to the matrix (e.g., epoxy) may be used. For example, 15-90% by weight of the backing layer 18 is formed from filler 19. In other examples, 20-40%, 50-70% or 70-80% is used.

Any ratios of the types of fillers 19 to another type of filler 19 may be used. For example, 25-30% or 15-35% rubber particles, 25-50% or 20-40% metal particles, and 20-50% or 25-40% ceramic particles by weight of filler.

The different ratios of fillers 19 tune various characteristics of the backing layer 18. Depending on the transducer and/or power levels to be used for transmission, backing layers 18 with different characteristics may be formed. By including three or more different types of filler material, the acoustic attenuation, thermal conductivity, and/or acoustic impedance may be tuned. Three or more different types of filler (e.g., rubber, metal, and ceramic in particular) may allow for beneficial values for two or more (e.g., all three) of the attenuation, thermal conductivity, and impedance characteristics. The acoustic attenuation is predominantly influenced by the rubber particles, any air gaps, and differences in velocity of the different materials. The thermal conductivity is predominantly influenced by the ceramic particles with a lesser contribution by the metal particles. The acoustic impedance is predominantly influenced by the metal particles due to higher density of metal as compared to the other types of materials.

In one embodiment, the backing has an acoustic attenuation of at least 2 dB/mm at 2.0 MHz or at least 5 dB/mm at 3.5 MHz, an acoustic impedance of at least 0.9 or 1 Mrayl, and a thermal conductivity of at least 3 W/mk. Table 1 shows some samples for filler combinations and corresponding characteristics.

TABLE 1

| Sample Code | Epoxy (gm) | | BYK (Drops) | Filler (grams) | | |
|---|---|---|---|---|---|---|
| | DER 332 | DEH24 | | Silicone | AlN | W |
| 1 | 11.78 | 1.62 | 4 | 15 | 18 | 30 |
| 2 | 11.78 | 1.62 | 4 | 22 | 18 | 30 |
| 3 | 11.78 | 1.62 | 4 | 29 | 18 | 30 |
| 4 | 11.78 | 1.62 | 4 | 35 | 17 | 16 |
| 5 | 11.78 | 1.62 | 4 | 30 | 17 | 16 |
| 8 | 11.78 | 1.62 | 4 | 30 | 30 | 30 |
| 9 | 11.78 | 1.62 | 4 | 25 | 30 | 30 |

DER 332 is an epoxy resin, DEH 24 is an epoxy curing agent, BYK is a surfactant, AlN is Aluminum nitride, and W is tungsten. These examples result in different characteristics of the backing, as shown in Table 2 below:

TABLE 2

| Sample Code | Density | Impedance | Velocity | Attenuation (dB/mm) | | | | |
|---|---|---|---|---|---|---|---|---|
| | | | | 1 | 1.5 | 2 | 2.5 | 3 |
| 1 | 2.366 | 3.53 | 1491.50 | 0.97 | 2.14 | 2.06 | 3.83 | 5.73 |
| 2 | 2.0556 | 2.60 | 1262.64 | 1.29 | 2.93 | 5.07 | 7.51 | 11.69 |
| 3 | 1.9031 | 1.95 | 1027.01 | 2.61 | 5.36 | 10.13 | 16.64 | 16.17 |
| 4 | 1.474 | 0.97 | 658.95 | 10.33 | 21.44 | | | |
| 5 | 1.5827 | 1.14 | 723.24 | 7.45 | 21.34 | | | |
| 8 | 1.7918 | 1.36 | 756.34 | 13.26 | 23.01 | | | |
| 9 | 1.981 | 1.74 | 877.73 | 7.36 | 15.95 | 27.77 | | |

Figure 2:
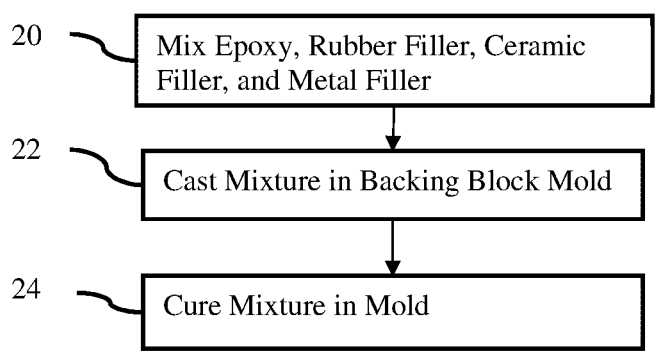
FIG. 2 is one embodiment of a method for forming a backing block of an ultrasound transducer.

FIG. 2 shows one embodiment of a method of forming an acoustic backing block for an acoustic transducer. Three or more types of material are used as filler for a composite backing block. The characteristics of the types of materials contribute to different aspects of the backing. By combining different types of filler, the acoustic and/or thermal characteristics of the backing block may provide for good attenuation and impedance in combination with good thermal conductivity.

The method forms the backing layer 18 of FIG. 1 for use with the transducer 10 of FIG. 1 but may be used to form other acoustic absorbers for other acoustic transducers.

Additional, different, or fewer acts may be provided. For example, acts for aligning with an array and/or bonding in an array stack are provided.

In act 20, a blender, vibrator (e.g., shaker), centrifuge, or other stirring device mixes a composite mixture. For example, the two parts of the epoxy (e.g., a thermoset and thermoplastic of the epoxy) and filler are placed into a vat. Additional, different, or fewer components may be added. The mixture in the vat is mixed by vibration, rotation, stirring, and/or another application of energy to homogenously distribute the different fillers.

The filler, such as rubber powder (e.g., silicone particles), ceramic powder (e.g., aluminum nitride particles), and metal powder (e.g., tungsten particles) are added separately or premixed. The types of filler are added separately in any order or are combined and then added to the epoxy. Any ratios, volume, and/or % weight of the different types of filler may be used. The components of the filler are measured and added.

The component ingredients to form the composite backing or acoustic absorber are mixed. Any mixing process may be used, including the order of adding, period of mixing, speed of mixing, temperature of mixing, pressure of mixing, humidity of mixing, or other controllable mixing characteristic. The mixing results in a slurry of composite or mixture.

In act 22, a robot, pump, and/or servo-controlled nozzle casts the mixture into a mold for an acoustic backing block. The mixture is poured, injected, extruded, or otherwise placed in the mold. In alternative embodiments, the mixture is manually poured into the mold.

The mold is shaped to form an acoustic absorber. The size and shape are based on the transducer or array for which the backing is being formed. Other parts to be fixed in the backing may also be included in the mold, such as wires and/or brackets. The mold may include indentations, extensions, and/or other shapes for aligning, machining, or using the backer once formed. In one embodiment, the mold defines a square or rectangular plate or slab with the length, width, and/or depth based on (e.g., matching a size and shape) a two-dimensional array of transducer elements. Alternatively, the shape and size are to provide a slab of acoustic absorber to be machined to the size and/or shape for use with a specific transducer.

In act 24, the mixture as cast into the mold is cured. The mold may be enclosed, such as covering an open top with a plate. The mold may be held still or moved (e.g., vibrated) during curing.

The curing is by chemical activation. The epoxy cures, becoming more solid or converting from a liquid form to a gel or solid form. Alternatively or additionally, heat, pressure, or other energy is added to speed the curing. In one embodiment, a clamp applies pressure to a top plate to assure size and flatness over 12 hours of curing at 70° Celsius. Other approaches, temperatures, or periods may be used. Variation in any curing characteristics over time as the slurry cures may be used.

After curing, the backing composite or acoustic absorber is removed from the mold. The backing may be machined, such as sanded, planed, cut, drilled, stamped, and/or otherwise altered for use. For example, a single plate of cured composite may be cut into multiple backing blocks for multiple transducers. Alternatively, a given cured composite from the mold is used for a single or given transducer.

In one embodiment, the required amount epoxy resin and hardener are weighed and placed into a mixing cup. The silicone powder, aluminum nitride powders and Tungsten are then added. This disposable cup is placed into centrifugal mixer for 3 min with 1500 RPM. The mixture is then removed and cast. This mold is placed under a press, and the press and mold are placed in air oven at 55 C overnight. The mold is removed and continues to cure for 12 hours.

The backing composite or acoustic absorber is positioned against or in a transducer stack (e.g., position against flexible circuit material providing the signal electrodes for the elements of the array). Using epoxy, clamping, and/or other connection, the backing is held in place against the transducer stack.

Once the transducer is formed (e.g., after bonding of the acoustic stack including the backing block and any kerfing), the transducer may be used. Due to the tuned acoustic impedance, acoustic attenuation, and thermal conductivity, the transducer may be used with additional power (e.g., overheats less rapidly) while providing sufficient noise reduction (e.g., absorbs undesired acoustic energy) and while avoiding reflection (e.g., impedance generally matches the transducer element). The combination of three or more types of filler material provides for the desired or tuned characteristics of the backing.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. An ultrasound transducer comprising:
an array of transducer elements, the transducer elements of the array operable separably for transducing between acoustic and electrical energies, the array having a face at which the acoustic energies are transmitted and received and a back opposite the face; and
a backing adjacent the back of the array, the backing comprising a composite of a base and filler comprising rubber particles, metal particles, and ceramic particles;
wherein the backing comprises an epoxy as the base with a substantially homogeneous distribution in the backing of each of the rubber particles, metal particles, and ceramic particles as the filler, a quantity of the homogenously distributed ceramic particles tuned relative to quantities of the homogenously distributed metal and rubber particles for thermal conductivity of the backing with the epoxy as the base; and
wherein the backing has an acoustic attenuation of at least 2 dB/mm at 2.0 MHZ, an acoustic impedance of at least 1 Mrayl, and a thermal conductivity of at least 3 W/mk.

2. The ultrasound transducer of claim 1 wherein the rubber particles comprises silicone powder.

3. The ultrasound transducer of claim 1 wherein the metal particles comprises tungsten powder.

4. The ultrasound transducer of claim 1 wherein the ceramic particles comprises aluminum nitride powder.

5. The ultrasound transducer of claim 1 wherein the backing comprises the filler of 25-30% rubber particles, 25-50% metal particles, and 20-50% ceramic particles by weight with a total of 100%.

6. The ultrasound transducer of claim 1 wherein the rubber particles are 8-100 micrometers and the metal particles are 10-60 micrometers.

7. The ultrasound transducer of claim 1 wherein the rubber particles, metal particles, and ceramic particles are 15-90% of a weight of the backing.

8. The ultrasound transducer of claim 1 wherein the backing comprises a molded block of acoustic absorber.

9. A composite acoustic absorber for an ultrasound transducer array, the composite acoustic absorber comprising:
cured epoxy;
rubber filler;
metal filler; and
ceramic filler;
wherein the rubber filler, metal filler, and ceramic filler are each distributed with a substantially homogeneous distribution in the cured epoxy, a quantity of the ceramic filler tuned relative to quantities of the metal and rubber fillers for thermal conductivity of the composite acoustic absorber with the cured epoxy as a base; and
wherein the distribution of the rubber, metal, and ceramic fillers in the cured epoxy provides an acoustic attenuation of at least 2 dB/mm at 2.0 MHZ, an acoustic impedance of at least 1 Mrayl, and a thermal conductivity of at least 3 W/mk.

10. The composite acoustic absorber of claim 9 wherein the rubber filler comprises silicone powder, the metal filler comprises tungsten powder, and the ceramic filler comprises aluminum nitride powder.

11. The composite acoustic absorber of claim 9 wherein the cured epoxy comprises a block shaped and sized to mate with an ultrasound transducer array.

12. The composite acoustic absorber of claim 9 wherein the cured epoxy comprises a matrix and wherein the rubber, metal, and ceramic fillers in the matrix form air gaps.

13. The composite acoustic absorber of claim 9 wherein the backing comprises 25-30% rubber particles as the rubber filler, 25-50% metal particles as the metal filler, and 20-50% ceramic filler as the ceramic filler by weight with a total filler of 100%.

14. A composite acoustic absorber for an ultrasound transducer array, the composite acoustic absorber comprising:
cured epoxy;
rubber filler;
metal filler; and
ceramic filler;
wherein the rubber filler, metal filler, and ceramic filler are each distributed with a substantially homogeneous distribution in the cured epoxy, a quantity of the ceramic filler tuned relative to quantities of the metal and rubber fillers for thermal conductivity of the composite acoustic absorber with the cured epoxy as a base; and
wherein the cured epoxy comprises a matrix and wherein the rubber, metal, and ceramic fillers in the matrix form air gaps.

15. The composite acoustic absorber of claim 14 wherein the rubber filler comprises silicone powder, the metal filler comprises tungsten powder, and the ceramic filler comprises aluminum nitride powder.

16. The composite acoustic absorber of claim 14 wherein the cured epoxy comprises a block shaped and sized to mate with an ultrasound transducer array.

17. The composite acoustic absorber of claim 14 wherein the distribution of the rubber, metal, and ceramic fillers in the cured epoxy provides an acoustic attenuation of at least 2 dB/mm at 2.0 MHZ, an acoustic impedance of at least 1 Mrayl, and a thermal conductivity of at least 3 W/mk.

18. The composite acoustic absorber of claim 14 wherein the backing comprises 25-30% rubber particles as the rubber filler, 25-50% metal particles as the metal filler, and 20-50% ceramic filler as the ceramic filler by weight with a total filler of 100%.

* * * * *